Oct. 1, 1946. E. PRUSHEK Plant Pat. 711
CHRYSANTHEMUM PLANT
Filed Nov. 28, 1945
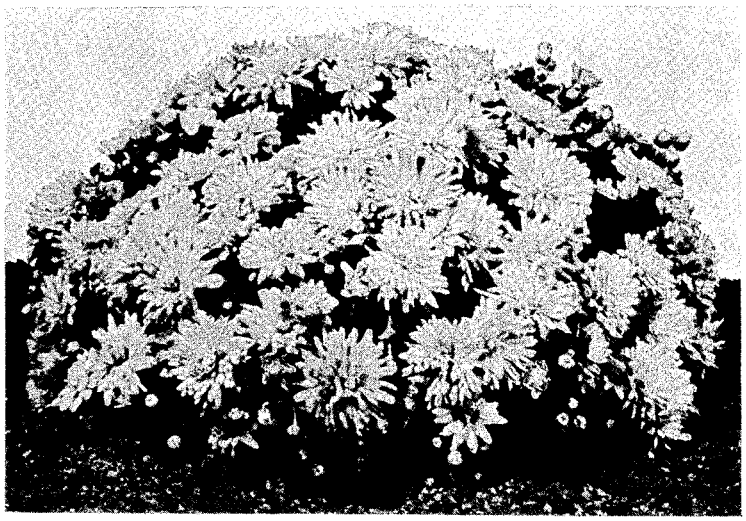
INVENTOR.
Emil Prushek
BY Robert Robb
Attorneys Patented Oct. 1, 1946

Plant Pat. 711

UNITED STATES PATENT OFFICE

711

CHRYSANTHEMUM PLANT

Emil Prushek, Berrien Springs, Mich., assignor to The R. M. Kellogg Company, Three Rivers, Mich., a corporation of Michigan Application November 28, 1945, Serial No. 631,249

1 Claim. (Cl. 47—60)

The present invention relates to a new and distinct variety of chrysanthemum plant, resulting from crossing the variety "Summer Sunset" and an unnamed seedling.

The present variety belongs to that class of hardy perennials which are typically noted for their dwarfish habit of growth, and the dominating features of distinction reside in the coloring character of the prolific blooms and the particular form of the plant.

With reference to the coloring, it is notable that between the opening bud stage and that of the faded flowers, there is a harmony of intense sunset colors over a long season. The accompanying drawing illustrates the variety in its prime.

As to plant form, unlike any other variety, it is very dwarf, compact and fluoriferous, making a small, rather flat, mound of color especially suitable for border or edging work. In height, it is only about one-third that of its diameter.

By way of comparison, the present variety most nearly resembles "Summer Sunset," one of its parents, but differs importantly therefrom in form and strength of coloring of the blossom at all seasons. Moreover, the plant is more dwarf, more compact and flatter. While the diameter is about half that of "Summer Sunset," the height is only about one-fourth that of the latter.

Asexual reproduction shows that these characteristics hold true through succeeding propogations.

The following is a detailed description of the new variety, color terminology being in accord with the Robert F. Wilson Horticultural Colour Chart, except where otherwise indicated to have ordinary dictionary significance:

Classification:

*Botanic.*—Chrysanthemum hortorum.

*Flower*

Blooming habit: Blooms early; profusely. Recurrent—continuous in the fall.

Bud:

*Size.*—Small. Is not affected by wet or hot weather.

Bloom:

*Size.*—Small. Average size when fully expanded, 1¼″.

*Borne.*—In flat clusters.

*Stems.*—Short; weak.

*Petalage.*—Double.

The following is a description of a newly opened flower:

*Dominant color.*—Center of flower—No separate center. Outer petals—Lilac Purple, Plate 031/2 or 031/1. Inner petals—Burnt Orange, Plate 014/1. Reverse of petals—Outer—Erythrite Red over Straw color. Erythrite Red, Plate 0027/1, streaks or shading. Inner—Same as outer reverse, but over a deeper Yellow.

*Discoloration.*—Flowers show no discernible variation from hour to hour during the day. However, over a period of ten days to fourteen days the flowers fade here and there to various shades of Yellow, Orchid, and Orange. These tones, while really due to fading, enhance the beauty of the flower-covered plant, giving it an opalescent effect. These shades are so various that it is impracticable to accurately list them all. Colors given according to the Chart are those of the flower in its prime.

*General tonality from a distance.*—When seen in the sunlight, the coloring of the flower has an iridescent effect, due to a blending of the Lilac Purple, Plate 013/2 or 013/1, of the outer rows of petals with the Burnt Orange, Plate 014/1, of the inner row of petals. Flower seems to take on luminosity in sunlight. In shade, the effect is about the same as just described, but not as luminous.

Petals:

*Texture.*—Thin; soft. Is not affected by wet or hot weather.

*Appearance.*—Inside and outside—shiny.

*Form.*—Long oval.

*Arrangement.*—Imbricated.

*Fragrance.*—Typical chrysanthemum.

*Lasting quality.*—On the plant, very long.

*Plant*

Form:

*Bush.*—Form and size of the plant are the important distinguishing characteristics. The plant forms a small, compact mound, almost completely covered with flowers, most similar in shape to Azaleamum "Summer Sunset," Plant Patent No. 561, but much smaller, and somewhat flatter. The main difference is size. Other Azaleamums grow to 2½ to 3½ feet across and 1 to 1½ feet high, while a typical specimen of the present variety grows to only 15″ across and 6″ to 8″ high. Most plants are very close to this size. Individual flowers are about the same form and size as "Summer Sunset."

Foliage:

*Size.*—Small.

*Quantity.*—Sparse.

*New foliage.*—Upper side—Normal Green; under side—Bright Green.

*Old foliage.*—Upper side—Dark Green; under side—Normal Green.

*Texture.*—Upper side—smooth; under side—smooth.

*Ribs and veins.*—Ordinary.

*Edge.*—Serrated; lobed.

*Serration.*—Single.

*Disease resistance.*—Resistant to leaf spot.

I claim:

A new and distinct variety of chrysanthemum plant characterized as to novelty by the intense coloring of blossoms, and the very dwarf, compact, rather flat form of the plant, substantially as shown and described.

EMIL PRUSHEK.